United States Patent
Waldman et al.

[11] Patent Number: 5,879,346
[45] Date of Patent: Mar. 9, 1999

[54] HAIR REMOVAL BY SELECTIVE PHOTOTHERMOLYSIS WITH AN ALEXANDRITE LASER

[75] Inventors: Amir Waldman, Hod Hasharon; Zvi Rozenberg, Mevasseret Zion; Ofer Braude, Ramat Gan; Michael Slatkine, Herzlia, all of Israel

[73] Assignee: ESC Medical Systems, Ltd., Yokneam, Israel

[21] Appl. No.: 767,886

[22] Filed: Dec. 17, 1996

Related U.S. Application Data

[63] Continuation-in-part of Ser. No. 729,240, Oct. 9, 1996, Pat. No. 5,868,732.

[60] Provisional application No. 60/008,802 Dec. 18, 1995.

[30] Foreign Application Priority Data

Nov. 8, 1996 [IL] Israel .......................................... 119051

[51] Int. Cl.[6] .................................................. A61B 17/36
[52] U.S. Cl. ..................................................................... 606/9
[58] Field of Search ............................ 606/9, 2–3, 10–13

[56] References Cited

U.S. PATENT DOCUMENTS

| | | |
|---|---|---|
| 3,538,919 | 11/1970 | Meyer et al. . |
| 3,693,623 | 9/1972 | Harte et al. . |
| 4,617,926 | 10/1986 | Sutton . |
| 4,693,244 | 9/1987 | Daikuzono . |
| 4,736,743 | 4/1988 | Daikuzono . |
| 5,046,810 | 9/1991 | Steiner et al. . |
| 5,057,104 | 10/1991 | Chess . |
| 5,059,192 | 10/1991 | Zaias . |
| 5,129,897 | 7/1992 | Daikuzono . |
| 5,133,709 | 7/1992 | Prince . |
| 5,139,495 | 8/1992 | Daikuzono . |
| 5,190,535 | 3/1993 | Daikuzono . |
| 5,217,455 | 6/1993 | Tan . |
| 5,226,907 | 7/1993 | Tankovich . |
| 5,250,068 | 10/1993 | Ideguchi et al. . |
| 5,269,777 | 12/1993 | Doiron et al. . |
| 5,282,797 | 2/1994 | Chess . |
| 5,290,273 | 3/1994 | Tan . |
| 5,344,418 | 9/1994 | Ghaffari . |
| 5,425,728 | 6/1995 | Tankovich . |
| 5,486,172 | 1/1996 | Chess . |
| 5,595,568 | 1/1997 | Anderson et al. . |
| 5,620,478 | 4/1997 | Eckhouse .................................. 607/88 |
| 5,647,866 | 7/1997 | Zaias et al. .................................. 606/9 |

FOREIGN PATENT DOCUMENTS

| | | |
|---|---|---|
| 0292621 | 11/1988 | European Pat. Off. . |
| 0514258 | 11/1992 | European Pat. Off. . |
| 2209577 | 3/1992 | Japan . |
| 2209578 | 3/1992 | Japan . |
| 2214084 | 8/1989 | United Kingdom . |
| 91/13652 | 9/1991 | WIPO . |
| 92/17243 | 10/1992 | WIPO . |

*Primary Examiner*—Michael Peffley
*Assistant Examiner*—Roy Gibson
*Attorney, Agent, or Firm*—Richard I. Samuel, Esq.; Friedman Siegelbaum

[57] ABSTRACT

Hair removal by using an Alexandrite laser emitting energy between 0.2–40 joules per pulse to provide an energy fluence between 15 and 70 joules per centimeter square and having a pulse duration of between 100 microseconds and 10 milliseconds. A scanner may be used to direct the laser beam on the tissue. The skin in the area to be irradiated may be shaved prior to exposure to laser treatment and may be also covered by a protective substance serving as a heat sink.

22 Claims, 10 Drawing Sheets

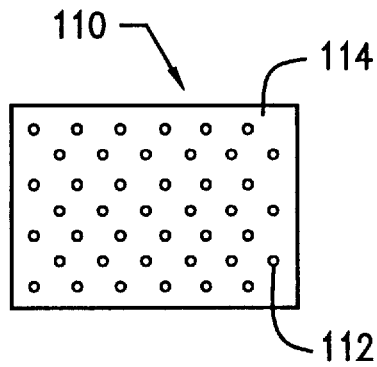 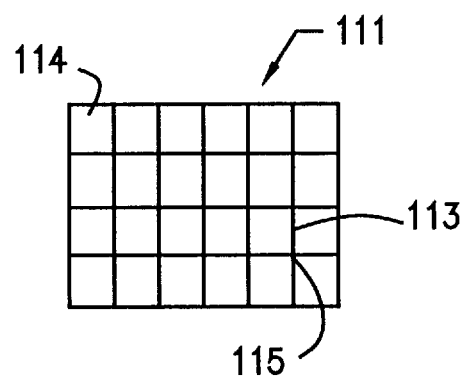
FIG. 9A  FIG. 9B
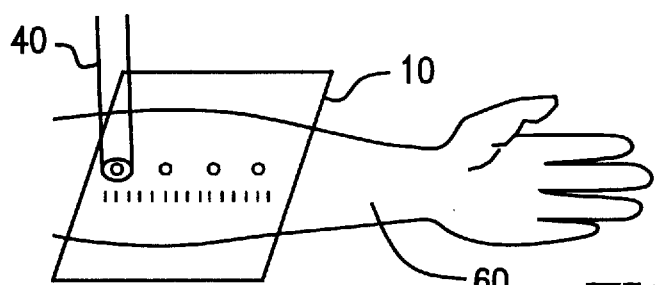
FIG. 10A
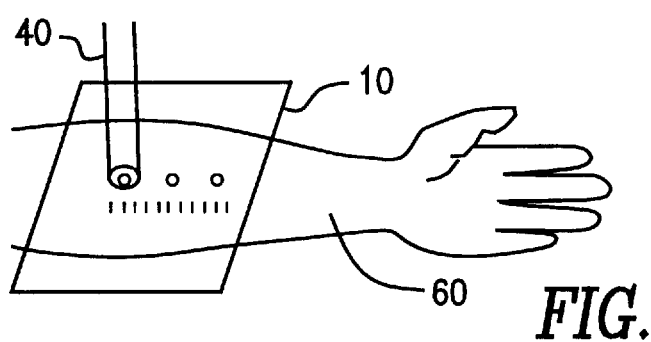
FIG. 10B
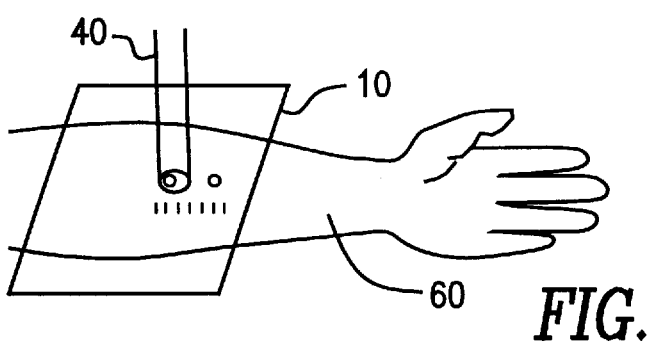
FIG. 10C

HAIR REMOVAL BY SELECTIVE PHOTOTHERMOLYSIS WITH AN ALEXANDRITE LASER

CROSS-REFERENCE TO COPENDING PATENT APPLICATIONS

This is a continuation-in-part of Ser. No. 08/729,240, filed Oct. 9, 1996, now U.S. Pat. No. 5,868,732, and entitled COOLING APPARATUS FOR CUTANEOUS TREATMENT EMPLOYING A LASER AND METHOD FOR OPERATING SAME, whose contents are incorporated herein by reference. Also incorporated herein by reference are the contents of application Ser. No. 08/769,492, filed Dec. 18, 1996, based on provisional patent application Ser. No. 60/008,802, filed Dec. 18, 1995 and entitled HAIR REMOVAL WITH A LASER SYSTEM AND WAVEGUIDE FOR RADIAL TRANSMISSION OF LASER ENERGY, from which priority is claimed.

FIELD OF THE INVENTION

The present invention relates to laser surgery apparatus and method to remove hair that directs pulsed laser beams from an Alexandrite laser to a protective substance that protects an external surface of skin against damage from overheating and that provides markings to indicate where the impingement takes place.

BACKGROUND OF THE INVENTION

Treatment of skin with lasers have been the subject of study since the early 1960s. A variety of lasers have been used in dermatologic practice. Different lasers are primarily distinguished by a wavelength of the light produced, measured in nanometers, such as the XeF excimer (351 nm), argon (488 nm, 514 nm), ruby (694 nm), Nd:YAG (1060 nm), and $CO_2$ (10,600 nm) lasers.

Photothermolysis of skin has been demonstrated using dye laser pulses and Q-switched ruby laser pulses. It has been found that radiation from Q-switched ruby lasers deeply penetrates the epidermis and dermis. It has also been found that application of ruby red laser energy can cause depigmentation of the skin as well as significant follicular damage to the extent that the hair will fall out.

The Q-switched ruby laser has been used for the treatment of tattoos, pigmented lesions, and conventional ruby lasers have been used to treat epidermal and dermal pigmented lesions. Studies based on experimentation with Q-switched ruby lasers, as well as other lasers, have reported skin depigmentation and temporary hair loss.

The use of lasers for non-invasive hair removal has been disclosed in U.S. Pat. No. 5,059,192, issued Oct. 22, 1991 to Nardo Zaias, entitled METHOD OF HAIR DEPILATION. This patent teaches the use of a pulsed ruby laser as the preferred embodiment. The ruby laser radiation (694 nm wavelength) penetrates deep into tissue and is relatively well absorbed by melanin to cause thermal damage to dark, melanin rich hair shafts and follicles.

U.S. Pat. No. 5,226,907, issued Jul. 13, 1993 to Nikoli Tankovich, entitled HAIR REMOVAL DEVICE AND METHOD and U.S. Pat. No. 5,425,728, issued Jun. 20, 1995 to Nikoli Tankovich, entitled HAIR REMOVAL AND METHOD teach the use of a $CO_2$ pulse laser and a Nd:YAG laser, among other types of lasers, to effect hair removal in conjunction with light absorbing oil used to stain hair.

The Nd:YAG laser is limited to relatively low energy levels at affordable commercial production costs. It is effective only for highly absorptive hairs, usually stained for this purpose. Energy levels adequate for hair removal with bare hairs makes it impractical to use an Nd:YAG laser.

Large pulsed ruby lasers are capable of delivering very high energy levels—as high as 40 J. As a result, they can attain the energy fluences of 15–70 $J/cm^2$ necessary for hair removal. However, ruby lasers can be fired only at a very low repetition rate—approximately 1 pulse per second (pps). This limits the benefit of using a scanner such as that described in U.S. Pat. No. 5,411,502 to Eliezer Zair and the computerized pulsed generator (CPG) scanner, commercially available from Coherent Inc. of California, USA. This low repetition rate is too low to cover large treated areas as legs and hands in a reasonable time. A 10×30 $cm^2$ area (one leg) would require some 1200 pulses, each pulse covering an area of 0.25 $cm^2$ (typical for hair removal with a 5 Joules laser). Assuming a repetition rate of 1 pps, this leads to 20 minutes for a single leg, or over 1 hour for two legs and two hands. This considerably limits the number of patients treatable for hair removal with the expensive laser.

Another drawback of pulsed ruby lasers is their limited pulse time duration. Ruby lasers operated in their free running modes can usually attain a maximum time duration of 300–1000 microseconds. Extending the pulse duration to 1–10 milliseconds is almost impractical. On the other hand, it would be desirable to operate ruby lasers at pulse durations of 1–10 milliseconds in most cases of hair removal because of hair follicle diameters being of over 100 microns.

A third drawback of ruby lasers is their size due to their low efficacy. A 5 Joules, 1 pps ruby laser may typically be of 150 cm×70 cm×70 cm size. A 25 Joule laser may weigh over 400 kilograms.

U.S. Pat. No. 5,290,273, issued Mar. 1, 1994 to Oon Tan, entitled LASER TREATMENT METHOD FOR REMOVING PIGMENT CONTAINING LESIONS FROM THE SKIN OF A LIVING HUMAN and U.S. Pat. No. 5,217,455, issued Jun. 9, 1993 to Oon Tan, entitled LASER TREATMENT METHOD FOR REMOVING PIGMENTATIONS, LESIONS, AND ABNORMALITIES FROM THE SKIN OF A LIVING PERSON, teach the use of an Alexandrite laser instead of a ruby laser to treat pigmentation, lesions and skin abnormalities. Both teach that before and after irradiation, the area irradiated should be checked for the presence or absence of adhexac (skin appendages) such as hairs. If a hair loss condition is observed, then the energy density from the laser radiation should be decreased for subsequent treatments. The pulse duration is 10–300 nanoseconds.

Skin treatment employing laser based systems, usually pulsed laser based systems is well known in the art. Such laser based systems are used inter alia for cutaneous vascular lesions treatment and for hair removal, the latter application being described for example in U.S. Pat. Nos. 5,059,192 to Zais and 5,226,907 to Tankovich.

As is also well known in the art, the operation of laser based systems for cutaneous treatment is more effective when the tissue is cooled. Examples for prior art devices for cooling the skin during laser treatment are U.S. Pat. No. 5,057,104, U.S. Pat. No. 5,282,797 and U.S. Pat. No. 5,486,172 to Chess specifically designed for cutaneous vascular lesions treatments and U.S. Pat. No. 5,344,418 to Ghaffari.

A major disadvantage of prior art laser based systems for cutaneous treatment is that the operation of the laser is not visible to the physician carrying the treatment, thus he can not be sure that the laser covered the entire area to be treated.

This results in an inhomogeneous treatment of the skin, such as an inhomogeneous removal of hair from the patient skin in the case of hair removal treatment.

SUMMARY OF THE INVENTION

One aspect of the invention is to generate at least one pulsed Alexandrite laser beam that travels in a path to a hair follicle. The beam is of sufficient energy and pulse duration to damage hair follicle papilla.

Another aspect of the invention is to provide a protective substance in the path to help protect an external surface of the skin against overheating otherwise arising from the pulsed laser beam.

For non-invasive surgery, this protective substance may be a cooling gel applied to the external surface of the skin to cool the external surface and thereby prevent overheating. For invasive surgery, this protective substance may be energy absorbing or reflecting particles that block the laser radiation from penetrating to the external surface of the skin.

Preferably, a plurality of markings are provided that indicate the locations on which the laser beam impinges. The markings may each vaporize upon impingement of a laser beam thereupon or be spaced away so that the laser beam will not impinge them.

The protective substance may cool the skin during laser treatment. This substance may be contained within an enclosure which in turn may have thereon the markings. The enclosure is flexible preferably formed substantially of polyethylene, polypropylene or polycarbonate. This enclosure may have a peelable cover so as to enable direct contact between the gel and the area of the skin of a patient. Preferably, the edge of the enclosure exposed by peeling the peelable cover includes an adhesive material for attaching the enclosure to the patient skin.

The markings may be physically placed on the area of the skin to be treated or adjacent thereto or the markings may be placed over the area of the skin to be treated such as on a transparent sheet disposed intermediate the laser beam and the skin. Alternately, the markings may be projected onto the area of the skin to be treated.

BRIEF DESCRIPTION OF THE DRAWINGS

For a better understanding of the present invention, reference is made to the following description and accompanying drawings, while the scope of the invention is set forth in the appended claims.

FIGS. 9A and 9B are schematic representations of arrangements showing a plurality of markings in accordance with two alternative embodiments of the invention;

FIGS. 10A–10C are schematic representations of progressive views illustrating the operation of the apparatus of FIG. 9A;

DESCRIPTION OF THE PREFERRED EMBODIMENT

Figure 1:
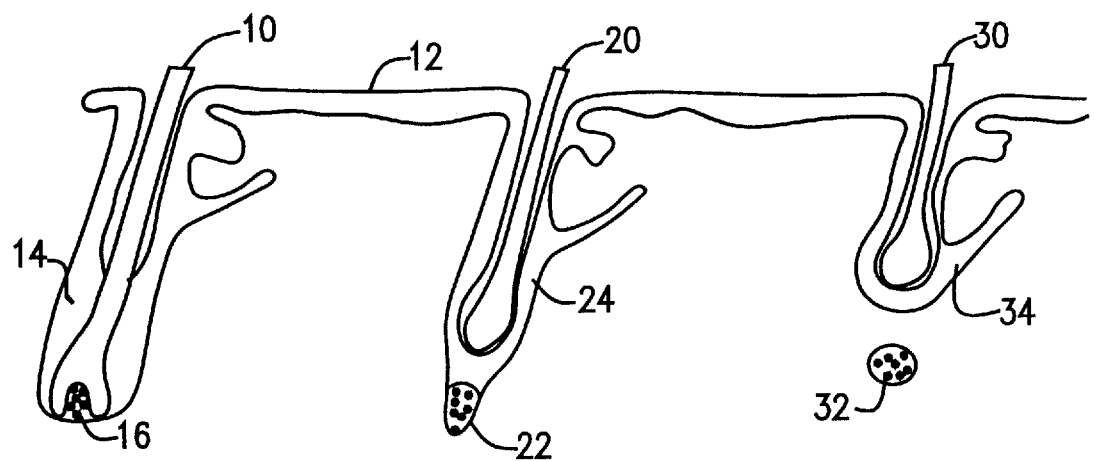
FIG. 1 is a cross-sectional view of three hair shafts showing the stages of the hair cycle.

FIG. 1 shows a hair shaft 10 which has been cut down near the surface of the skin 12. The shaft 10 extends down to the follicle 14 which at the anagen stage of the hair cycle joins the papilla 16. Destruction of the papilla 16 is necessary to prevent hair regrowth.

After growing for a period of time that is different for different parts of the human body in the anagen stage, the hair shaft 10 enters the catagen stage represented by hair shaft 20 wherein the papilla 22 separates from the base of the follicle 24. The catagen stage lasts only a few weeks.

Hair shaft 30 represents the telogen stage of the hair cycle wherein the papilla 32 completely separates from the follicle 34 and forms a new secondary hair germ which will repeat the cycle. The telogen stage also lasts for a period of time that depends on the part of the body. For arms, it is about three months.

To assure sufficient injury to the papilla 32 at the telogen stage as well as the papilla 16 at the anlagen stage, use of a laser with sufficient energy and depth of penetration is necessary to achieve sufficient melanosomal destruction. Cutting of the hair shaft down to the skin 12 in advance of lasing provides two important functions of the treatment process. First, the tip 18 of the hair shaft 10 allows the laser operator to position the laser substantially vertically over the hair follicle opening such that an optimum location for aiming the laser pulse to strike the papilla 16 is obtained. Second, the reduction of excess hair eliminates additional scattering and absorption of other radiant energy contained in the pulse.

Figure 2:
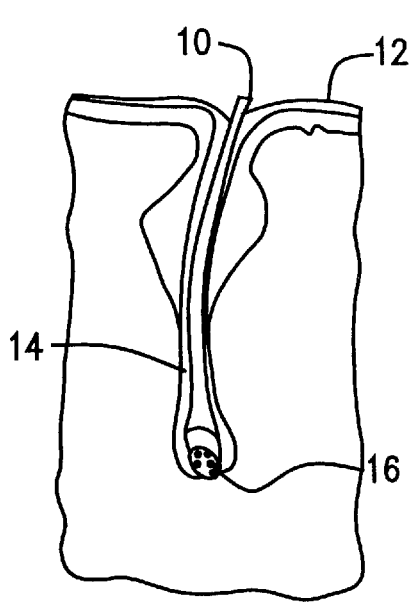
FIG. 2 is a cross-sectional view of a hair follicle after the top has been cut, but prior to application of laser pulse.

FIG. 2 shows an enlarged view of the hair shaft 10 prior to treatment, wherein the follicle 14 and papilla 16 are normal in appearance in the anlagen stage.

Figure 3:
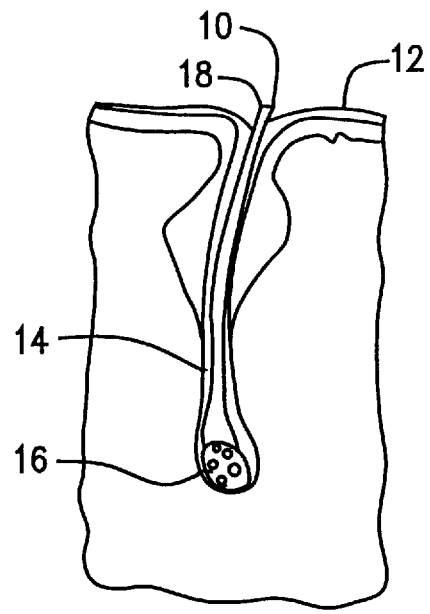
FIG. 3 is a cross-sectional view of the follicle of FIG. 2 after laser treatment, showing the damaged hair germ.

FIG. 3 shows the treatment after the laser pulse has been applied to the follicle 14 and the resulting effect on the papilla 16.

Application of the laser pulse to the follicle and the papilla causes photothermolysis which provides melanosomal disruption, including vaporization of the melanin in the follicle 14 and papilla 16, as well as vacuolation, edema, gas bubbles and protein denaturation. When the pulse applied is of sufficient energy level, these effects seriously injure the hair follicle and papilla, thereby damaging the hair germ which causes hair regrowth. The hair follicle 14 may extend into the reticular dermis up to 3 mm from the skin surface.

Figure 4:
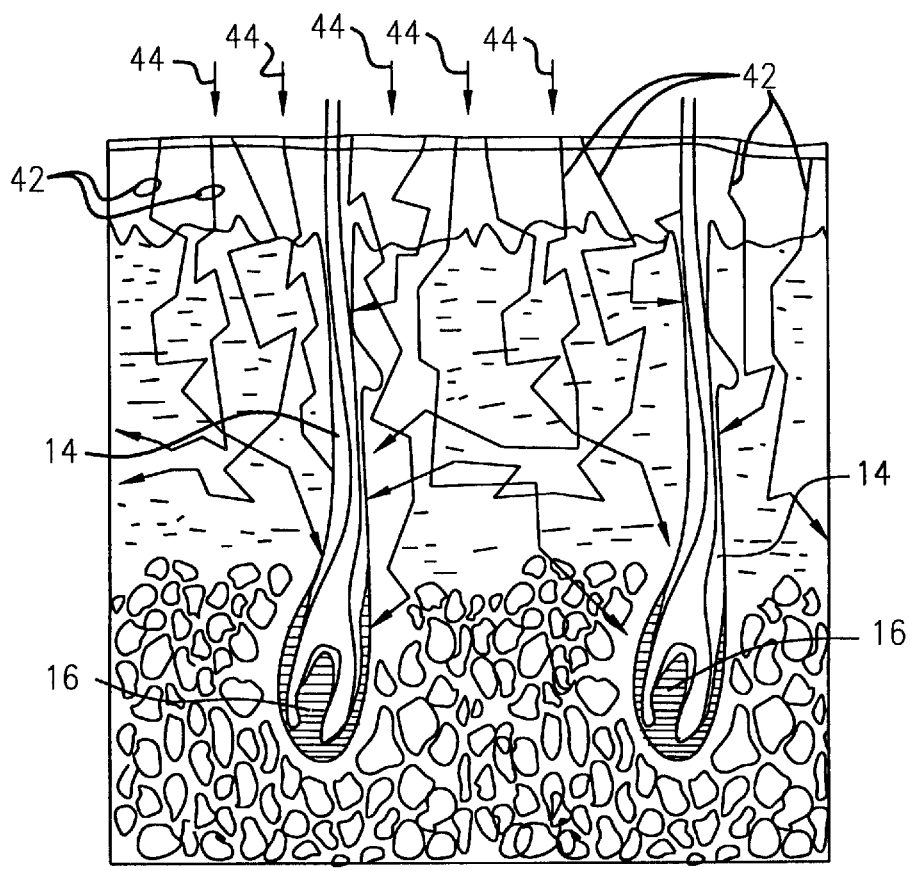
FIG. 4 is a schematic representation showing the impingement and skin penetration with an Alexandrite laser beam in effecting hair removal.

Turning to FIG. 4, the use of an Alexandrite laser beam 44 (see FIG. 7) is shown for non-invasive hair removal by selective photothermolysis.

In accordance with the process of selective photothermolysis, the pulse duration time should be shorter than the thermal relaxation time of the follicle. The thermal relaxation time is defined as the time it takes for a structure to cool to 50% of its peak temperature immediately after laser exposure. The calculated thermal relaxation time for hair shafts and follicle has been found to be approximately 1–10 milliseconds.

Figures 5A, 5B:
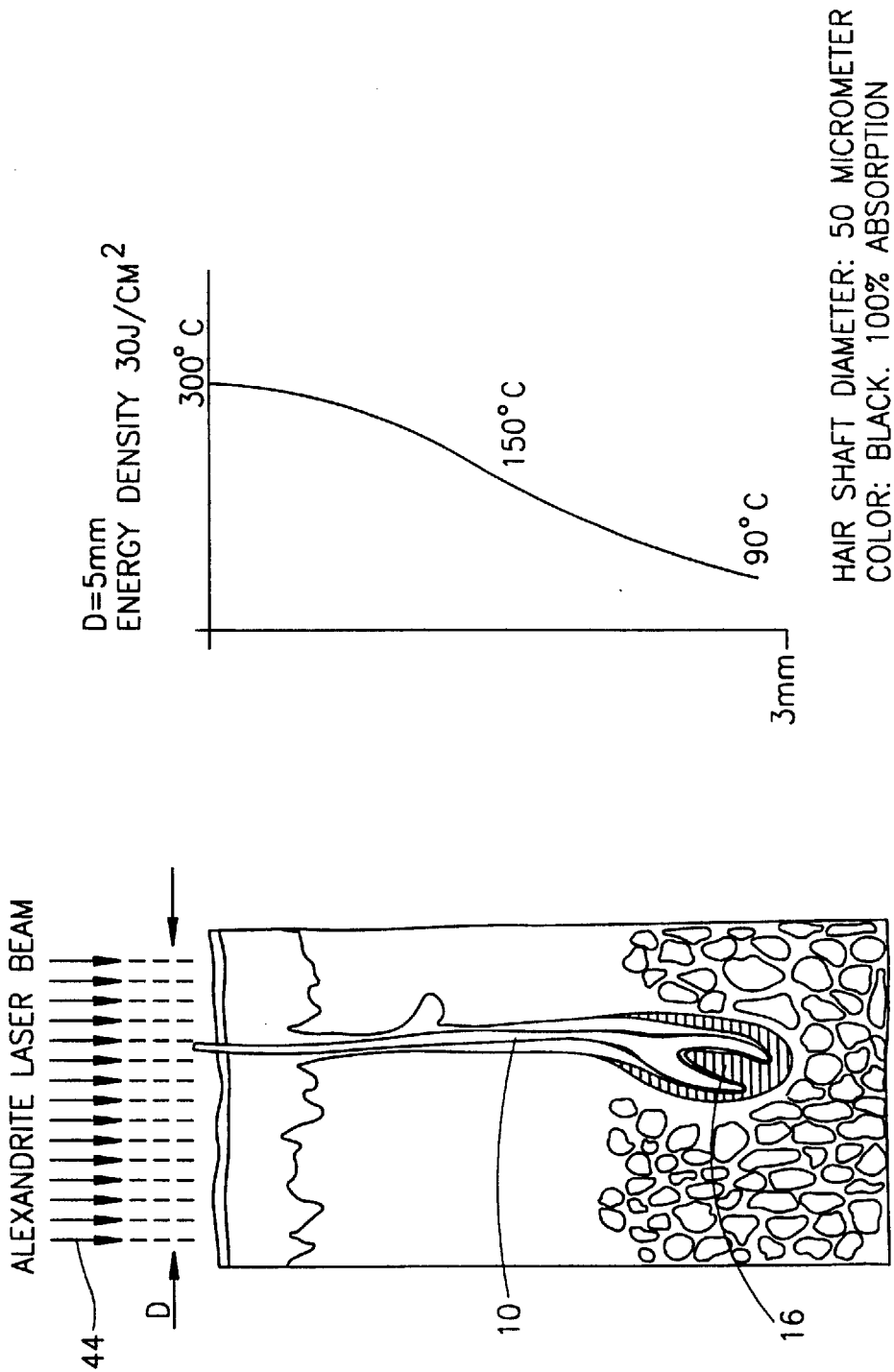
FIG. 5A shows a schematic pictorial representation of a hair follicle.
FIG. 5B shows a graph representing the results of a computer simulation of photothermolysis with an Alexandrite laser beam, aligned with the follicle of FIG. 5A.

FIG. 5 shows a computer simulation that is based on a "MONTE CARLO" statistical model of light scattering in the skin, see M.J.C. Van Germet et al., "Skin Optics", IEEE translation on Biomedical Engineering, Vol. 36, pp. 1146–1150 (1989). The temperature distribution shows follicle destruction.

Different types of hair and hair color will require variations in the energy dosage to effect permanent hair removal. Generally, darker hair will induce higher light absorption, therefore a lower dosage may be required.

Figure 6:
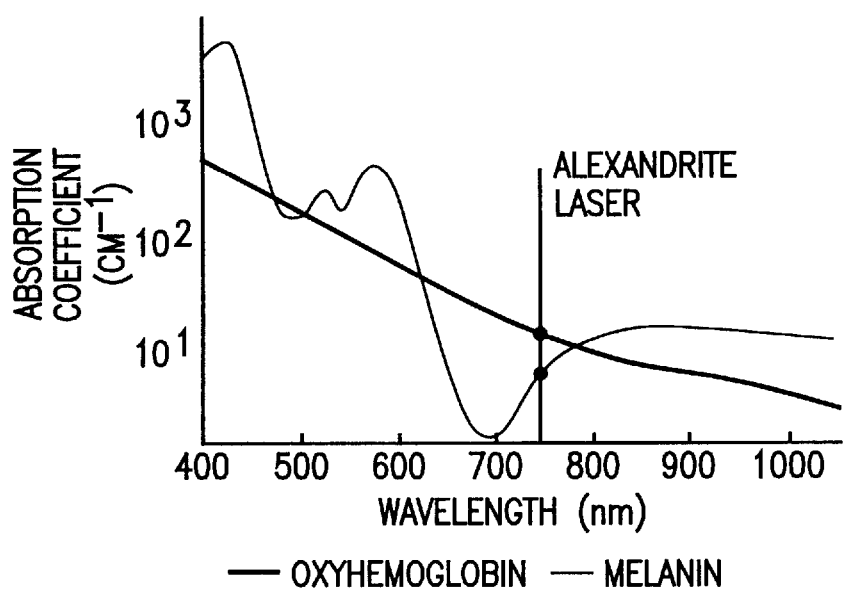
FIG. 6 is a graphical representation of the absorption spectrum of melanin and oxyhemoglobin.

As shown graphically in FIG. 6, the Alexandrite laser emits radiation at 755 nm. Its emitted beam absorption in tissue is higher than with a ruby laser (approximately 4 times higher). As a result, general tissue heating is higher, which may necessitate tissue cooling in contrast to the case of superficial heating with a ruby laser. Also, melanin absorption of Alexandrite laser radiation is lower than for ruby laser radiation, thus reducing the amount of hair shaft heating and thus laser effectiveness. However, such advantages of the ruby laser tissue effects over the Alexandrite laser tissue effects is offset by the very high energy levels attainable with small size, high repetition rate Alexandrite lasers.

According to an alternative embodiment of the present invention, the Alexandrite laser energy is absorbed at least partly by a stain added to the hair itself or by a stained lotion introduced into the hair follicle. The stain or stained lotion absorbs in the 755 nm wavelength. Such a stain or stained lotion may, for instance, be black or blue but not the color of the Alexandrite frequency of near infrared.

The following table provides a qualitative comparison between Alexandrite and ruby laser for use for hair removal.

QUALITATIVE COMPARISON BETWEEN ALEXANDRITE AND RUBY LASER FOR HAIR REMOVAL

TECHNOLOGY

| | RUBY | ALEXANDRITE |
|---|---|---|
| LASER COLOR | RED (694 NM) | INFRARED (755 NM) |
| ENERGY PER PULSE WITH A SMALL-MEDIUM SIZE LASER | LOW | HIGH |
| MAXIMUM PULSE DURATION IN FREE RUNNING MODE | UP TO 1 MILLISECOND (PRACTICAL) | LONGER (BETTER FOR HAIR REMOVAL) |

QUALITATIVE COMPARISON BETWEEN ALEXANDRITE AND RUBY LASER FOR HAIR REMOVAL

TISSUE INTERACTION

| | | |
|---|---|---|
| HAIR REMOVAL | GOOD | GOOD |
| DAMAGE TO EXTERNAL SKIN LAYER | HAVE TO BE CAREFUL WITH DARKER SKIN | SMALLER RISK TO DAMAGE DARKER SKIN - HIGHER ABSORPTION BY BLOOD VESSELS |

TREATMENT STRATEGY AND ECONOMY

| | | |
|---|---|---|
| USE OF A SCANNER | NO NEED; MANUAL WORK | ADVANTAGEOUS |
| COOLING REQUIREMENT | STRINGENT ONLY FOR EPIDERMIS | CONSIDERABLY LESS STRINGENT FOR EPIDERMIS. NEED FOR DERMIS |
| SPEED OF PROCEDURE | VERY SLOW | VERY FAST |
| POSSIBLE NUMBER OF PATIENTS PER DAY | SMALL | LARGE |

Figure 7:
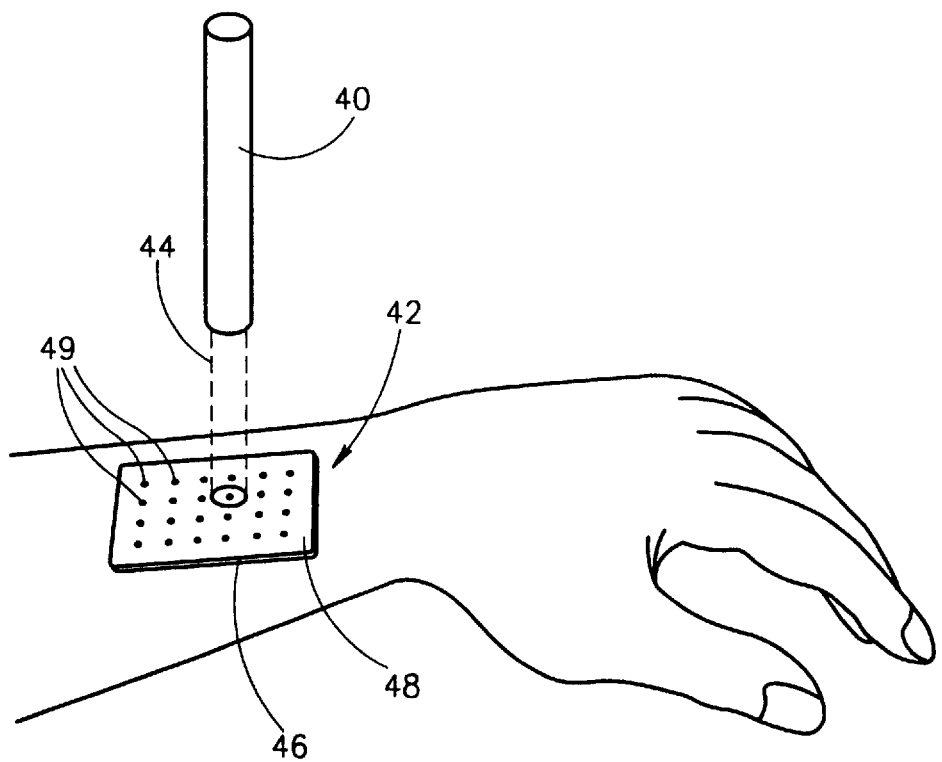
FIG. 7 is a schematic representation of the beam of an Alexandrite laser interacting with tissue in accordance with the invention.

Turning to FIG. 7, the laser delivery system 40 delivers a fast repetition rate pulses of laser radiation to the tissue that has been previously shaved. Preferably, the laser beam strikes the surface of the tissue substantially at a perpendicular angle thereto.

In accordance with the preferred embodiment, provision is made to protect the skin from overheating due to radiation from pulsed laser beams. A protective substance, such as a cooling substance contained in a cooling apparatus 42, is arranged on the skin, interposed between the skin and the laser beams.

The cooling apparatus 42 is placed on the tissue to cool the tissue that is being exposed to irradiation from a high average power Alexandrite laser beam 44. High average power arises from high energy per pulse and high frequency of the pulse repetition rate. In a preferred embodiment, the cooling apparatus includes a gel 46 of a matching optical index of refraction to that of a operative dyed transparency 48 having died dots 49 thereon and covering gel 46. The gel 46, when spread over the skin, should have a minimum thickness of 2–3 millimeters to be effective in protecting the external surface of the skin for about a 50–100 micron depth against overheating from pulsed laser beams. The gel 46 acts as a heat sink, withdrawing heat accumulating in the external surface of skin from the laser energy.

Figure 8:
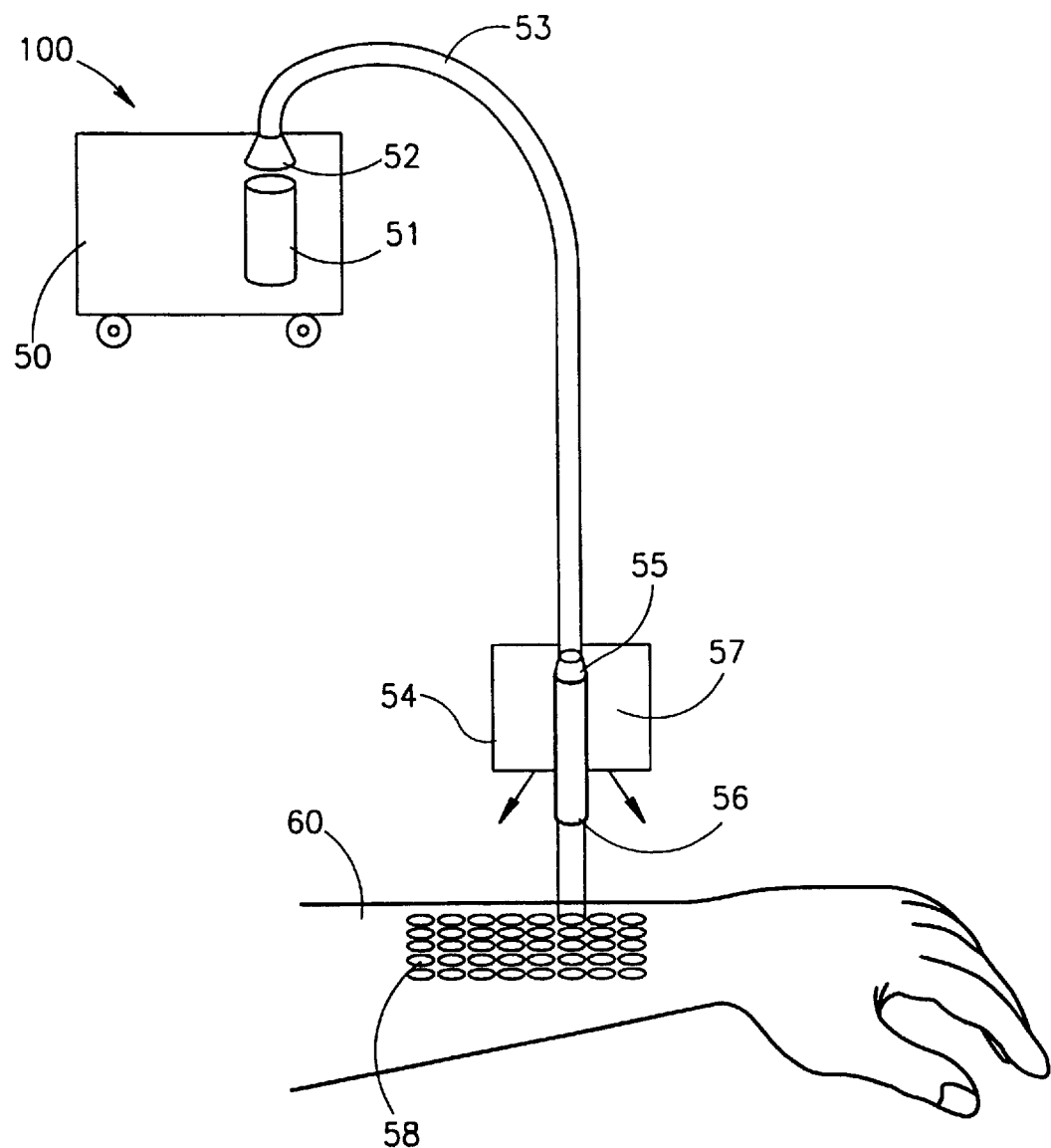
FIG. 8 is a schematic representation of an Alexandrite laser apparatus for hair depilation according to the present invention.

FIG. 8 illustrates a preferred embodiment of an Alexandrite laser apparatus 100 that comprises an Alexandrite laser source 50 including a conventional Alexandrite laser head 51 and a conventional coupling lens 52, a conventional optical fiber 53 connecting the Alexandrite laser source 50 to a conventional pulsed laser beam director 54 that has an imaging lens 55 and an aperture 56 through which the laser radiation is applied. In the preferred embodiment, apparatus 100 also includes a scanner 57 that causes the laser beam to sweep a pattern on the tissue being irradiated so as to irradiate spots 58 on the tissue. Spots 58 may coincide in registry with marks 48 of the cooling apparatus 42.

FIG. 8 also illustrates a modification of the embodiment of FIG. 4. As in the case of the FIG. 4 embodiment, the tissue 60 is shaved to cut hairs otherwise protruding from the surface of the tissue.

The following parameters are recommended for an Alexandrite laser with a fiber delivery system to remove hair from human beings:

Energy Level: within 100 mJ–20 J/Pulse, optimally 10 J/Pulse

Repetition Rate: 10 Pulse per second

Pulse Duration: 100 microseconds to 3 milliseconds, possibly to 10 milliseconds

Spot Size on Tissue: 4–10 mm.

Energy Fluence: 15–70 J/cm$^2$

Tissue Cooling: 4° C.

Based on clinical trials with fifty patients on faces, arms, legs, the acceptable results were observed where the hair diameters ranged between 40 microns to 80 microns. These results are for a single treatment of the arm:

30% growth of hairs after 3 months @ 50 J/cm$^2$
50% growth of hairs after 3 months @ 37 J/cm$^2$
70% growth of hairs after 3 months @ 25 J/cm$^2$ In the case of two treatments, in some cases only 15% growth was observed after 3 months. Another effect observed during clinical trials is that for the case of some hair growth, the diameter of the hair is about 25 percent smaller than the original. That is, the treatment causes shrinkage in the hair diameter.

Reference is now made to FIGS. 9A and 9B which illustrate an apparatus having a plurality of markings thereon for tracking a laser beam as it sweeps across tissue, e.g., to remove hairs from a patient's skin. The markings indicate whether the laser beam actually reached a location on the skin corresponding to each marking.

FIG. 9A shows a pattern 110 that comprises a plurality of markings 112 which are preferably, but not necessarily, ordered equidistant from each other. The markings 112 may be black dots that vaporize upon impingement of the laser beam thereupon. FIG. 9B shows a pattern 111 that comprises a grid 113 with each grid junction 115 being analogous to the markings 112. Alternatively, the markings 112 or grid junctions 115 may be arranged so that the laser beam will not be directed to impinge them, e.g., may be spaced neighboring the areas to be impinged.

Figure 11B:
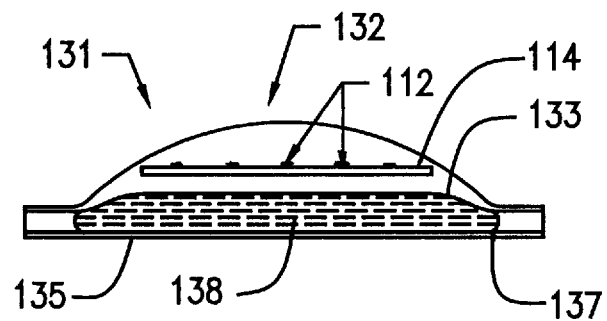
FIG. 11B is a schematic representation of a cooling apparatus in accordance with another embodiment of the invention.
Figure 12:
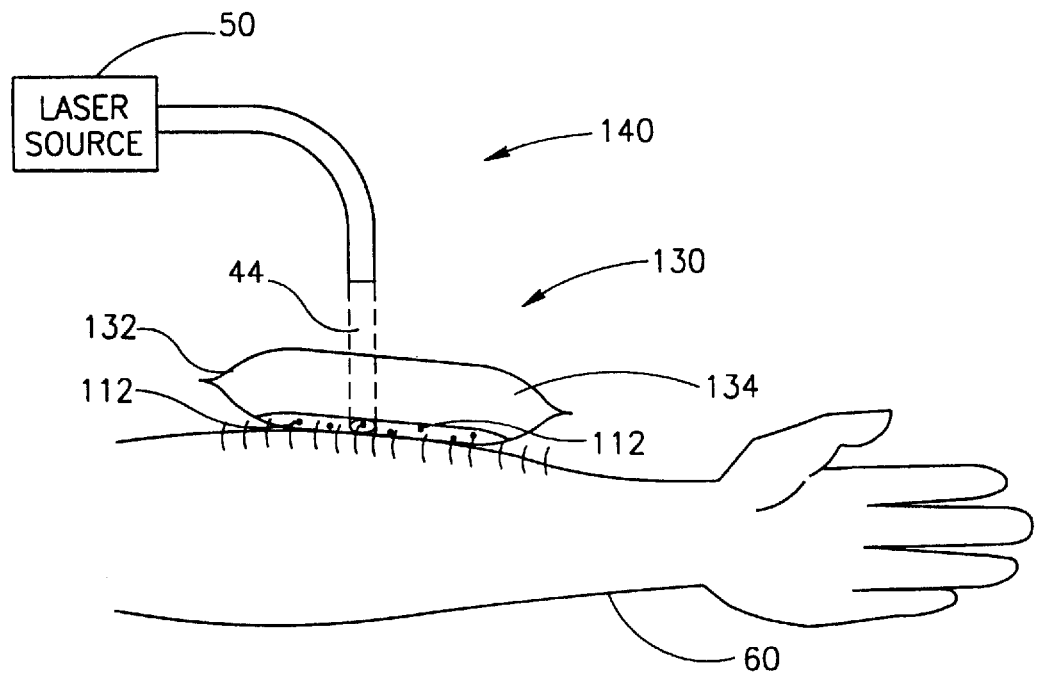
FIG. 12 is a schematic representation of a system for hair removal in accordance with still another embodiment of the invention.

In the embodiments of FIGS. 9A and 9B, patterns 110 and 111, respectively, are each on a respective sheet 114 of transparent material. The transparent material may be polyethylene, polypropylene or polycarbonate. The markings 112 and grid 113 are each made of any suitable identifier, such as ink printed on the sheet 114. In a further embodiment of the present invention, patterns 110 and 111 form part of a cooling apparatus as depicted in FIGS. 11B and 12. In yet a further embodiment of the present invention, markings 112 are marked on the skin. In yet another embodiment, the markings are projected on the skin as illustrated with respect to FIG. 13.

FIGS. 10A–10C illustrate the progression of the treatment over time with each successive laser pulse directed to a corresponding successive marking 112 so as to vaporize the markings 112 and the associated hairs 124 thereunder by scanning the laser beam across the tissue 60. After pulsing the laser source 50 a desired number of times onto all the markings 112 or grid junctions 115, substantially full coverage of the area to be treated is attained. In an alternative embodiment, the markings 112 or the grid 113 are used to indicate the vicinity and not the exact location on which the laser beam impinges and therefore are not being vaporized by impingement of the laser beam thereupon. The sheet 114 is placed intermediate the laser source 50 and the patient's tissue 60. Preferably, the sheet extends substantially parallel to the skin tissue 60.

Figure 11A:
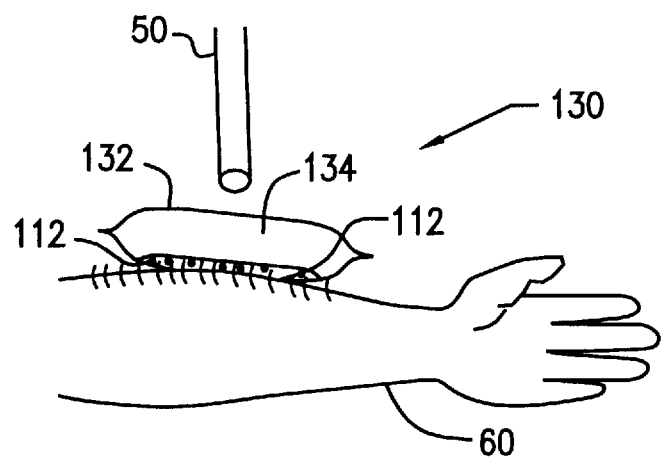
FIG. 11A is a schematic representation of a cooling apparatus in accordance with an embodiment of the invention.

Referring now to FIG. 11A, the pattern 110 is illustrated as part of a cooling apparatus 130 so as to further increase the effectiveness of the laser treatment. While the cooling apparatus 130 may be any prior art cooling apparatus, in a preferred embodiment of the present invention, the cooling apparatus 130 comprises a flexible enclosure 132 formed of a relatively thin plastic material, such as polyethylene, polypropylene or polycarbonate, having therein any suitable cooling substance 134. An example of the cooling substance 134 is water, preferably with salt, to decrease its freezing temperature. A transparent sheet 114 with the markings 112 is disposed in enclosure 132 as shown in FIG. 11B. This cooling substance 134 helps protect the skin from thermal damage otherwise arising from pulsed laser beams used in hair removal.

A particular feature of the present invention is the use of an ultrasound gel 138, such as the Aquarius 101 Ultrasound gel, commercially available from Meditab Ltd. of Israel. Gel 138 is disposed intermediate the tissue 60 and the cooling apparatus 130. Since enclosure 132 is flexible it is more easy to handle and to place over tissue 60 than a conventional cooling apparatus that is rigid. However, since enclosure 132 need not be necessarily in direct contact with the skin, gel 138 provides the required optical index of refraction matching between the skin and cooling apparatus 130.

According to an alternative preferred embodiment of the present invention illustrated in FIG. 11B, a cooling apparatus 131 is substantially similar to the cooling apparatus 130 and therefore similar elements are referenced in FIGS. 11A and 11B by the same reference numerals. Cooling apparatus 131 differs from cooling apparatus 130 in that it also includes gel 138 enclosed within an enclosure 133 having peelable cover 135. In operation, peelable cover 135 is peeled and cooling apparatus 131 is attached to the skin with attachments 137. Preferably, the edge of the enclosure 133 exposed by peeling the peelable cover includes an adhesive material which serves as the attachment 137 for attaching the cooling apparatus to the patient's skin.

Cooling apparatus 130 and cooling apparatus 131 are used in conjunction with a laser based skin treatment system, generally referenced 140, illustrated in FIG. 12. Although FIG. 12 is described with respect to cooling apparatus 130, it is equally applicable to cooling apparatus 131.

System 140 includes a laser source 50 operating to provide a pulsed laser beam 44 onto a cooling apparatus 130 and gel 138. In operation, the gel 138 is spread over the area of the skin to be treated and cooling apparatus 130 is placed thereon intermediate gel 138 and laser source 50. A physician (not shown) then operates to treat the skin with the pulsed laser beam 44 as described hereinabove with reference to FIGS. 10A through 10C.

Figure 13:
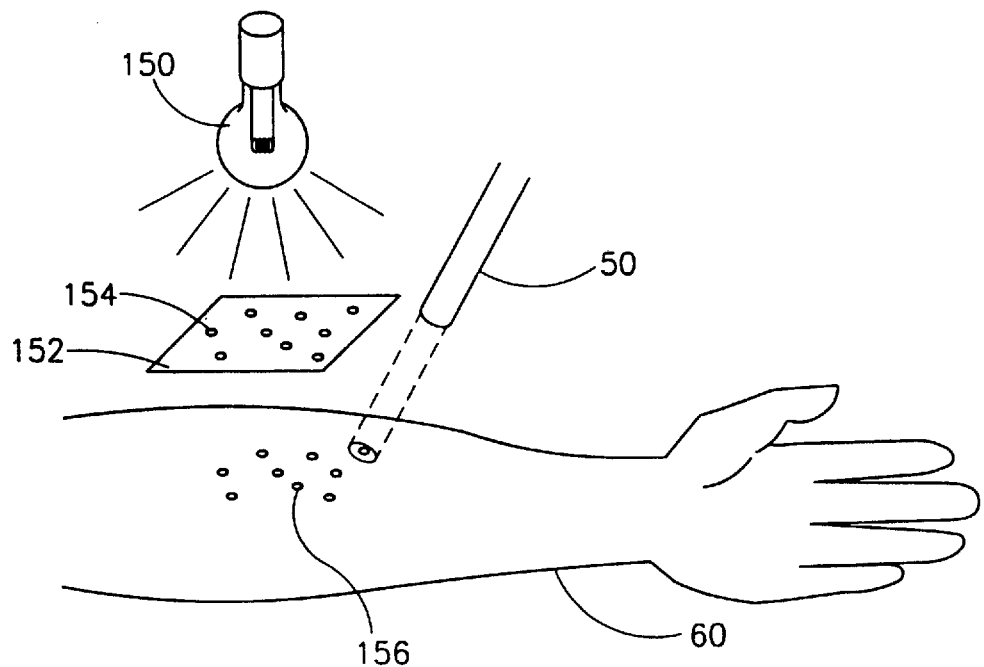
FIG. 13 is a schematic representation of a marking projection system in accordance with a further embodiment of the invention.

While the present invention has been described with respect to markings 112, it is equally applicable to grid junctions 115. Yet another example is to employ a projection apparatus in order to project the markings of the treated area as illustrated in FIG. 13. FIG. 13 shows a light source 150 that projects light through a transparent sheet 152 having markings 154 thereon so as to effectively mark tissue 60 with shade markings 156. Laser 50 operates in the same manner as previously discussed.

Figure 14A:
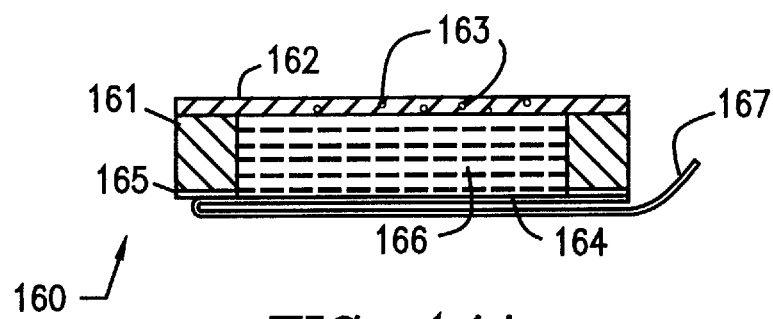
FIG. 14A is a schematic representation of a cooling apparatus in accordance with yet another embodiment of the invention.

FIG. 14A shows a cooling apparatus 160 in which the markings are part of the enclosure and not of a marking disposed therein. The cooling apparatus 160 of FIG. 14A comprises an enclosure 161 of which the top part 162 faces away from the skin during operation. The cooling includes discrete marks 163 or a grid thereon and of which the bottom part is a folded removable cover 164. This cover 164 is removed after the cooling apparatus 160 is attached to the skin with attachments 165. Disposed in enclosure 161 is a gel 166 that is used as the cooling agent during operation of the laser on the skin.

Figure 14B:
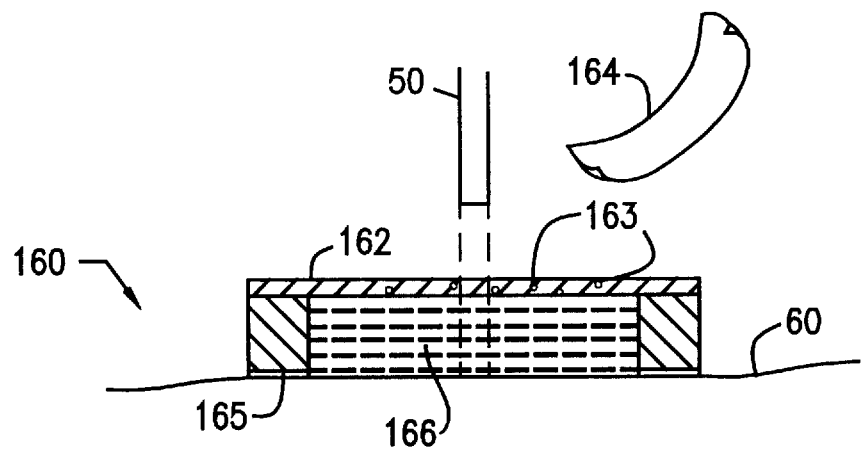
FIG. 14B illustrates the cooling apparatus of FIG. 14A in operation.

In operation, apparatus 160 is placed on the skin and a peelable cover is pulled out by pulling its edge 167. The gel 166 thereby comes into contact with the area to be treated as shown in FIG. 14B and the laser beam is directed onto the treated area bearing the indicia of the plurality of markings 163.

In an alternative embodiment, the peelable cover 164 is removed before the cooling apparatus 160 is tied to the skin.

While the foregoing description and drawings represent the preferred embodiments of the present invention, it will be understood that various changes and modifications may be made without departing from the spirit and scope of the present invention. For example, a colored marking at the edge of any cooling apparatus, such as cooling apparatus 160 may be added such that the cooling apparatus marks the area being treated.

For purposes of interpretation of the claims, "markings" covers any form of point indicia, whether ink dots, grid junctions, surface contour indentations or protrusions, etc.

The present invention clearly covers non-invasive hair removal by selective photothermolysis with an Alexandrite laser. However, it also pertains to invasive hair removal with an Alexandrite laser in that a protective substance, such as energy absorbing particles in lotion, fills the hair follicle and effectively blocks laser energy emitting from an invasive laser probe from penetrating to the external layer of the skin. These energy absorbing particles may be carbon black or white reflective that keep the laser energy contained to the hair follicle. In both the invasive and non-invasive techniques, the concept is to pulse the Alexandrite laser and rely on the protective substance to protect the skin against overheating. In this manner, scarring of surrounding tissue from the pulsed laser beam is minimized.

While the foregoing description and drawings represent the preferred embodiments of the present invention, it will be understood that various changes and modifications may be made without departing from the spirit and scope of the present invention.

What is claimed is:

1. A laser surgery apparatus to remove hair, comprising:
   an Alexandrite laser that generates at least one pulsed laser beam that travels in a path and of sufficient energy and pulse duration to damage a hair follicle;
   a protective substance arranged in said path to help protect an external surface of the skin against overheating otherwise arising from the pulsed laser beam; and
   a transparent sheet arranged in said path and bearing non-transparent markings that are arranged to provide an indication of where the pulsed laser beam passes through said protective substance, whereby hair follicles that are in the path become damaged by the at least one pulsed laser beam.

2. An apparatus as in claim 1, wherein each of said markings is constructed of a material that vaporizes in response to impingement by the pulsed laser beam.

3. An apparatus as in claim 1, wherein said markings are responsive to impingement by the pulsed laser beam to provide the indication.

4. An apparatus as in claim 1, wherein said markings are selected from the group consisting of inks and light projections.

5. An apparatus as in claim 1, wherein said protective substance is an ultrasound gel.

6. A laser surgery apparatus to remove hair, comprising:
   an Alexandrite laser that generates at least one pulsed laser beam that travels in a path and of sufficient energy and pulse duration to damage hair follicle;
   a protective substance arranged in said path to help protect an external surface of the skin against overheating otherwise arising from the pulsed laser beam; and
   a projector that projects markings that are arranged to provide an indication of where the pulsed laser beam passes through said protective substance onto the protective substance by shining light through a transparent sheet having markings.

7. A laser surgery apparatus to remove hair, comprising:
   an Alexandrite laser that generates at least one pulsed laser beam that travels in a path and of sufficient energy and pulse duration to damage hair follicle;
   a protective substance arranged in said path to help protect an external surface of the skin against overheating otherwise arising from the pulsed laser beam; and
   an enclosure containing said protective substance, said enclosure being interposed in said path;
   wherein said enclosure includes a plurality of sheets of transparent material.

8. An apparatus as in claim 7, wherein said sheets are constructed of a plastic material selected from the group consisting of polyethylene, polypropylene, polycarbonate, and any combination thereof.

9. An apparatus as in claim 7, further comprising an ultrasound gel within said enclosure.

10. An apparatus as in claim 7, wherein said enclosure is flexible.

11. A method of laser surgery to remove hair, comprising:
    generating at least one pulsed laser beam that travels in a path from an Alexandrite laser and of sufficient energy and pulse duration to damage a hair follicle;
    interposing a protective substance in the path to help protect an external surface of the skin against overheating otherwise arising from the pulsed laser beam; and
    indicating with markings where the pulsed laser beam passes through the protective substance, whereby hair follicles that are in the path become damaged by the at least one pulsed laser beam.

12. A method as in claim 11, wherein said markings vaporize in response to the pulsed laser beam impinging said markings.

13. A method as in claim 11, wherein the step of indicating includes projecting the markings by shining light at the protective substance through a transparent sheet with markings.

14. A method as in claim 11, wherein the step of indicating arises in response to the pulsed laser beam impinging the markings.

15. A method as in claim 11, wherein the protective substance is an ultrasound gel.

16. A method as in claim 11, further comprising
    enclosing the protective substance in an enclosure, the enclosure being transparent; and
    flexing said enclosure.

17. A method as in claim 11, further comprising the step of keeping the path away from the markings at all times.

18. A method of hair removal, comprising the step of applying at least one Alexandrite laser pulse to at least one hair follicle, said Alexandrite laser pulse having sufficient pulse duration and radiant exposure dose of sufficient energy to damage said at least one hair follicle so that percentage hair growth diminishes and scarring of the surrounding skin is minimized
    wherein the step of applying provides an energy fluence on the tissue substantially in the range 25 to 50 J/cm$^2$ that results in a percentage growth of hairs after 3 months that is in accordance with a relationship between percentage growth after 3 months and energy fluence, the relationship being characterized by a curve profile whose coordinates include:

30% growth of hairs after 3 months @ 50 J/cm$^2$
50% growth of hair after 3 months @ 37 J/cm$^2$
70% growth of hairs after 3 months @ 25 J/cm$^2$.

19. A method of hair removal, comprising the steps of:

applying at least one Alexandrite laser pulse to at least one hair follicle, said Alexandrite laser pulse having sufficient pulse duration and radiant exposure dose of sufficient energy to damage said at least one hair follicle so that percentage hair growth diminishes and scarring of the surrounding skin is minimized; and shaving the hair before the step of applying so that the hair does not protrude from the skin to a position that would scatter radiant energy from the laser pulse upon impingement.

20. An apparatus for hair removal, comprising:

a. an Alexandrite laser source for generating at least one alexandrite laser pulse having a sufficient pulse duration and radiant exposure dose of sufficient energy to damage at least one hair follicle so that percentage hair growth diminishes and scarring of the surrounding skin is minimized; and b. a laser beam director that directs said laser pulses to said at least one hair follicle, wherein said laser beam director is adapted to be aligned over said at least one hair follicle opening in tissue, said beam director having an aperture of sufficient area to surround said at least one hair follicle and overlie its papilla so that said at least one pulse of laser radiation is directed through said aperture to said at least one hair follicle.

21. An apparatus for hair removal, comprising:

a. an Alexandrite laser source for generating at least one alexandrite laser pulse having a sufficient pulse duration and radiant exposure dose of sufficient energy to damage at least one hair follicle so that percentage hair growth diminishes and scarring of the surrounding skin is minimized;

b. a laser beam director that directs said laser pulses to said at least one hair follicle; and c. staining means for deploying any one of stain or stained lotion so as to absorb at least part of said at least one laser pulse.

22. An apparatus for hair removal, comprising:

a. an Alexandrite laser source for generating at least one alexandrite laser pulse having a sufficient pulse duration and radiant exposure dose of sufficient energy to damage at least one hair follicle so that percentage hair growth diminishes and scarring of the surrounding skin is minimized; and b. a laser beam director that directs said laser pulses to said at least one hair follicle, wherein said laser source is adapted to provide a level of energy fluence on the tissue substantially in the range of 25 to 50 J/cm$^2$ that results in a percentage growth of hairs after 3 months that is in accordance with a relationship between percentage hair growth after 3 months and energy fluence, the relationship being characterized by a curve profile whose coordinates include:

30% growth of hairs after 3 months @ 50 J/cm$^2$
50% growth of hairs after 3 months @ 37 J/cm$^2$
70% growth of hairs after 3 months @ 25 J/cm$^2$.

* * * * *